United States Patent
Boyd et al.

(10) Patent No.: US 7,020,511 B2
(45) Date of Patent: Mar. 28, 2006

(54) METHOD FOR THREE DIMENSIONAL CINE EBA/CTA IMAGING

(75) Inventors: Douglas P. Boyd, Hillsborough, CA (US); Susan E. Candell, Lafayette, CA (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 288 days.

(21) Appl. No.: 10/064,756

(22) Filed: Aug. 14, 2002

(65) Prior Publication Data

US 2003/0161436 A1   Aug. 28, 2003

Related U.S. Application Data

(60) Provisional application No. 60/358,888, filed on Feb. 22, 2002.

(51) Int. Cl.
   *A61B 5/05* (2006.01)
(52) U.S. Cl. ............. 600/428; 600/407; 600/410; 600/413; 600/415; 600/425; 600/476; 600/479; 378/4; 378/10; 378/12; 378/14; 378/19; 378/20; 378/21; 378/114; 378/115; 378/450; 378/483

(58) Field of Classification Search ............ 600/407, 600/425, 428, 410, 415, 476, 479, 450, 483, 600/413; 378/4, 10, 12, 14, 21, 20, 114, 378/115, 19
See application file for complete search history.

(56) References Cited

U.S. PATENT DOCUMENTS

| | | | | |
|---|---|---|---|---|
| 4,352,021 A | * | 9/1982 | Boyd et al. | 378/12 |
| 4,547,892 A | * | 10/1985 | Richey et al. | 378/8 |
| 5,594,772 A | * | 1/1997 | Toki et al. | 378/114 |
| 5,601,084 A | * | 2/1997 | Sheehan et al. | 600/450 |
| 6,154,516 A | * | 11/2000 | Heuscher et al. | 378/15 |
| 6,393,091 B1 | * | 5/2002 | Slack et al. | 378/8 |
| 6,510,337 B1 | * | 1/2003 | Heuscher et al. | 600/428 |
| 2003/0128801 A1 | * | 7/2003 | Eisenberg et al. | 378/19 |

* cited by examiner

*Primary Examiner*—Brian L. Casler
*Assistant Examiner*—Baisakhi Roy
(74) *Attorney, Agent, or Firm*—McAndrews, Held & Malloy, Ltd.; Peter J. Vogel; Michael A. Dellapenna

(57) ABSTRACT

Certain embodiments of the present invention provide a method for three-dimensional cine EBA/CTA imaging. The method includes monitoring a cardiac cycle of a patient and selecting a trigger point along the cardiac cycle. When the cardiac cycle of the patient reaches the trigger point, a computed tomography (CT) scan of the patient is initiated. At least two CT scans of the patient are performed during a time period over two or more cardiac cycles. A cine angiography image is constructed from the at least two CT scans.

33 Claims, 13 Drawing Sheets

Sweep Map: EBA

| Sweep | 1 | 2 | 3 | 4 | 5 | 6 | 7 | 8 |
|---|---|---|---|---|---|---|---|---|
| sweep | 1 | 2 | 3 | 4 | 5 | 6 | 7 | 8 |
| coll | 3 | 3 | 3 | 3 | 3 | 3 | 3 | 3 |
| mA | 1000 | 1000 | 1000 | 1000 | 1000 | 1000 | 1000 | 1000 |
| kV | 140 | 140 | 140 | 140 | 140 | 140 | 140 | 140 |
| Det | 3 | 3 | 3 | 3 | 3 | 3 | 3 | 3 |
| Type | 3 | 3 | 3 | 3 | 3 | 3 | 3 | 3 |
| Horiz | 400 | 400 | 400 | 400 | 397 | 397 | 397 | 397 |
| Vert | 210 | 210 | 210 | 210 | 210 | 210 | 210 | 210 |
| Slew | 0 | 0 | 0 | 0 | 0 | 0 | 0 | 0 |
| Tilt | 0 | 0 | 0 | 0 | 0 | 0 | 0 | 0 |
| Table Incr | 0 | 0 | 0 | 0 | 0 | 0 | 0 | 0 |
| Target | 3 | 3 | 3 | 3 | 3 | 3 | 3 | 3 |
| Trigger | (5,1,7,5,9) | (0) | (0) | (0) | (4,8,5,9) | (0) | (0) | (0) |
| Delay | (5,0.16,0,0.3) | (0) | (0) | (0) | (4,0.25,0,0.3) | (0) | (0) | (0) |

500

600

700

800

32 levels; 3 phases 32 levels; All phases

METHOD FOR THREE DIMENSIONAL CINE EBA/CTA IMAGING

CROSS REFERENCE TO RELATED APPLICATIONS

The present application relates to, and claims priority from, co-pending application Ser. No. 10/06757 filed on the same date as the present application and entitled "Method and Apparatus for Cine EBA/CTA Imaging". The present application relates to, and claims priority from, U.S. Provisional Application No. 60/358,888, filed on Feb. 22, 2002, and entitled "Cine EBA/CTA". The co-pending application and provisional application name Susan Candell and Douglas Boyd as joint inventors and are incorporated by reference herein in their entirety including the specifications, drawings, claims, abstracts and the like.

BACKGROUND OF THE INVENTION

The present invention generally relates to Computed Tomography Angiography (CTA)/Electron Beam Angiography (EBA). In particular, the present invention relates to cardiac cine imaging using CTA/EBA.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient. The generated images may be used for many purposes. For instance, internal defects in an object may be detected. Additionally, changes in internal structure or alignment may be determined. Fluid flow within an object may also be represented. Furthermore, the image may show the presence or absence of components in an object. The information gained from medical diagnostic imaging has applications in many fields, including medicine and manufacturing.

Angiography refers to techniques for imaging arteries in a body. Coronary arteries of the heart are some of the more significant arteries that are commonly imaged. Problems with coronary arteries account for a large percentage of deaths in the United States each year. Coronary arteries are difficult to image because coronary arteries move with a cardiac cycle with speeds of up to 20 millimeters per second. Observing motion of the coronary arteries may be helpful in diagnosing illnesses or defects.

During the past several years, CTA and EBA were developed to replace invasive coronary angiography. Coronary angiography uses direct injections of contrast media into the coronary arteries using a long catheter. CTA and EBA, on the other hand, use a less invasive approach of a simple intravenous injection of a contrast agent. Current methods obtain CT images of the coronary arteries at specific phases of the cardiac cycle. Since the CT images are obtained at a specific phase of the cardiac cycle using current methods, the CT images are stationary images. The stationary images form cross sectional CT images of coronary arteries. The cross section CT images may be combined to form a spatially three-dimensional image. The cross section images may be combined using techniques such as maximum intensity MIP, Volume Rendering (VR), Shaded Surface Display (SSD), or other types of image processing. The resulting three-dimensional image illustrates a stationary volume at one instant in time.

The images are formed from data acquired during a series of scan. In order for useful data to be acquired in a scan, data acquisition has been synchronized with the cardiac cycle. Gating refers to synchronizing data acquisition with the cardiac cycle. A wave of an electrocardiogram (ECG) may be used to "gate" or synchronize acquisition data with the cardiac cycle. There are two common types of gating, namely prospective and retrospective gating. Prospective gating triggers the start of axial scanning by monitoring the patient's ECG wave and anticipating a chosen point in the interval between R-wave peaks (R-to-R interval) in an ECG cycle. The chosen point may be selected to correspond to the region of the cardiac cycle where cardiac motion is at a minimum. Retrospective gating uses continuous scanning and selects particular images based on the ECG wave information. Conventional systems use retrospective gating for single static images.

Several conditions impact scanning and image acquisition. A typical patient may hold his or her breath for about 45 seconds. To minimize motion artifacts and generate an accurate image, it is preferable in conventional systems that an entire image series be scanned during one breath. Thus, a need exists for an imaging system that may capture imaging data fast enough to scan an entire series of cardiac images in one breath. Additionally, heart rates vary from patient to patient such as from about 50 beats per minute (slow), or 1.2 seconds/heartbeat, to about 120 beats per minute (pediatric), or 0.5 seconds/heartbeat. Current systems are incapable of easily adjusting for multiple or varied heart rates. The inability to adjust for multiple heart rates may result in image artifacts or in an inability to capture properly image data. Thus, there is a need for an imaging system that supports a full range of heart rates.

Further, a particular patient's heart rate may vary during an imaging series. For example, a heart rate may start at about 70 beats per minute, then reduce to 60 beats per minute when a patient first holds his or her breath, and then increase to 90 beats per minute at the end of a patient's ability to hold his or her breath. Also, a particular patient's heart rate may change from one heartbeat to another heartbeat due to stress and other factors. A changing heart rate may introduce motion artifacts or other image artifacts into the obtained images. Thus, there is a need to accommodate a changing heart rate. Furthermore, there is a need to detect irregular heartbeats.

Motion of a table or other apparatus used to position a patient may cause discomfort to a patient. Fast motion of a table may be uncomfortable to a patient and may also cause motion artifacts. Thus, a system is needed that reduces patient discomfort and motion artifacts in resulting images.

Heretofore, CTA and EBA systems have been unable to obtain moving images of the coronary arteries and more generally moving angiography. A series of images (2-D or 3-D) illustrating changes in an object with respect to time is referred to as a cine image. Conventional CTA and EBA systems have been unable to offer cine angiography. Thus, there is a need for an angiography imaging method and apparatus for reconstructing a sequence of two- or three-dimensional images that show the motion of coronary arteries during a cardiac cycle. Additionally, current imaging methods require a lengthy period to acquire images. The time period required to acquire coronary arterial images is often too lengthy for the comfort of a patient. Thus, a need exists for a method and apparatus for imaging coronary artery motion and cardiac activity in a short time window for accurate imaging and patient comfort. Further, current imaging methods result in gaps and poor resolution in the resulting three-dimensional image due to the reconstruction techniques used, such as retrospective gating and other image reconstruction techniques, for example. Thus, there is a need for an imaging method and apparatus for improved quality imaging for angiography and motion in a cardiac cycle.

SUMMARY OF THE INVENTION

Certain embodiments of the present invention provide a method for three-dimensional cine EBA/CTA imaging. The method includes monitoring a cardiac cycle of a patient and selecting a trigger point along the cardiac cycle. When the cardiac cycle of the patient reaches the trigger point, a computed tomography (CT) scan of the patient is initiated using a CT scanner. At least two CT scans of the patient are performed during a time period over two or more cardiac cycles. A cine angiography image is constructed from the at least two CT scans. Each scan may contain sufficient information to create a complete image.

In certain embodiments, the at least two CT scans are obtained during a single cardiac cycle of the patient. Alternatively, the at least two CT scans may be obtained consecutively and beginning at different points within the time period. In certain embodiments, multiple parallel CT slices are obtained from separate parallel rows of detectors in the CT scanner. In certain embodiments, a complete CT scan is performed in no more than 100 milliseconds.

In certain embodiments, an electron beam is swept across a target ring to perform the at least two CT scans. In certain embodiments an x-ray fan beam is utilized to obtain the at least two CT scans. In certain embodiments, the patient is moved with respect to the CT scanner between or during CT scans. Additionally, the patient may be moved with respect to the CT scanner during each of the at least two CT scans to obtain spiral scans.

In certain embodiments, a series of three dimensional images obtained may be combined into a three dimensional cine loop based on the at least two CT scans. The series of moving three dimensional images may also be displayed and/or stored.

BRIEF DESCRIPTION OF DRAWINGS

FIG. 4 illustrates an example of a sweep map, which describes a scanning series in a sweep-by-sweep format in accordance with certain embodiments of the present invention.

Figure 1:
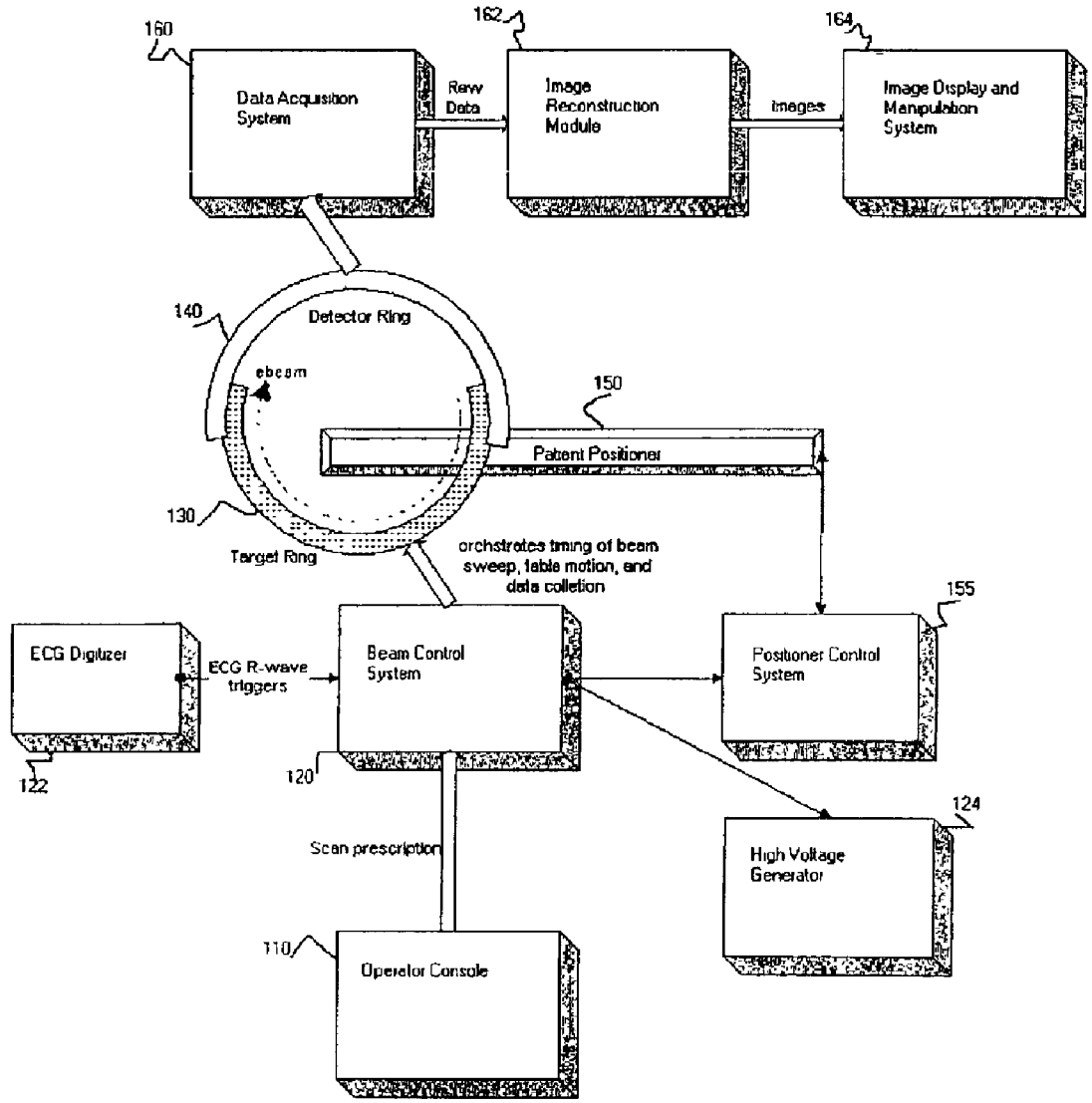
FIG. 1 illustrates an EBT imaging system in accordance with an embodiment of the present invention.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION

For the purpose of illustration only, the following detailed description references certain embodiments of an Electron Beam Tomography (EBT) imaging system. It is understood that the present invention may be used with other imaging systems, such as conventional computed tomography systems and other medical diagnostic imaging systems, for example.

FIG. 1 illustrates an EBT imaging system 100 in accordance with an embodiment of the present invention. The system 100 includes an operator console 110, a beam control system 120, an ECG digitizer 122, a high voltage generator 124, a target ring 130, a detector ring 140, a patient positioner 150, a positioner control system 155, a data acquisition system (DAS) 160, an image reconstruction module 162, and an image display and manipulation system 164.

The operator console 110, ECG digitizer 122, high voltage generator 124, and positioner control system 155 communicate with the beam control system 120 to generate and control an energy beam, such as an electron beam, for example. The beam control system 120 communicates with the positioner control system 155 to control the patient positioner 150. The beam control system 120 causes the electron beam to sweep over the target ring 130. A sweep may be a single traversal of the target ring 130. The detector ring 140 receives radiation, such as x-ray radiation, for example, from the target ring 130. The DAS 160 receives data from the detector ring 140. The DAS 160 transmits data to the image reconstruction module 162. The image reconstruction module 162 transmits images to the image display and manipulation system 164. The components of the system 100 may be separate units, may be integrated in various forms, and may be implemented in hardware and/or in software.

The operator console 110 selects a mode of operation for the system 100. The operator console 110 may also input parameters or configuration information, for example, for the system 100. The operator console 110 may set parameters such as triggering, scan type, electron beam sweep speed, and patient positioner 150 position (for example, horizontal, vertical, tilt, and/or slew), for example. An operator may input information into the system 100 using the operator console 110. Alternatively, a program or other automatic procedure may be used to initiate operations at the operator console 110. The operator console 110 may also control operations and characteristics of the system 100 during a procedure.

Based on operator input, the operator console 110 transmits operating information such as scanning mode, scanning configuration information, and system parameters, for example, to the beam control system 120. The ECG digitizer 122 transmits electrocardiogram R-wave trigger signals to the beam control system 120 to assist in timing of electron beam sweep and patient positioner 150 motion. An electrocardiogram (ECG) is a tracing of variations in electrical potential of a heart caused by excitation of heart muscle. An ECG includes waves of deflection resulting from atrial and ventricular activity changing with charge and voltage over time. A P-wave is deflection due to excitation of atria. A QRS complex includes Q-, R-, and S-waves of deflection due to excitation and depolarization of ventricles. A T-wave is deflection due to repolarization of the ventricles. Certain embodiments of the system 100 utilize the R-wave, an initial upward deflection of the QRS complex, for use in beam control and imaging. The ECG digitizer 122 transmits ECG R-wave triggers to the beam control system 120 to assist in controlling the electron beam and imaging sweeps.

The system 100 is configured to begin and end an imaging sweep at predetermined points along an R-wave. Imaging sweeps in the system 100 may also be triggered at predetermined points during the interval between R-waves (the R-to-R interval) or between R-wave peaks, for example. Alternatively, sweeps may be triggered based on a predetermined time interval after a reference point in time, for example. The trigger points may be set by the operator console 110.

The high voltage generator 124 may be used by the beam control system 120 to produce an electron beam. The high voltage module 124 may be a Spellman power supply with a power-on time of 80 or 130 milliseconds, for example.

The electron beam is focused and angled towards the target ring 130. The electron beam is swept over the target ring 130. When the electron beam hits the target ring 130, the target ring 130 emits a fan beam of radiation, such as x-rays, for example. The target ring 130 may be made of tungsten or other metal, for example. The target ring 130 may be shaped in an arc, such as in a 210-degree arc. Each 210-degree sweep of the electron beam over the target ring 130 produces a fan beam, such as a 30-degree fan beam, of electrons from the target ring 130.

The x-rays emitted from the target ring 130 pass through an object, such as a patient, for example, that is located on the patient positioner 150. The x-rays then impinge upon the detector ring 140. The detector ring 140 may include one, two or more rows of detectors that generate signals in response to the impinging x-rays. The signals are transmitted from the detector ring 140 to the DAS 160 where the signals are acquired and processed.

Data from the detector ring 140 signals may then be sent from the DAS 150 to the image reconstruction module 162. The image reconstruction module 162 processes the data to construct one or more images. The image or images may be stationary image(s), motion image(s), or a combination of stationary and motion (cine) images. The image reconstruction module 162 may employ a plurality of reconstruction processes, such as backprojection, forward projection, Fourier analysis, and other reconstruction methods, for example. The image(s) are then transmitted to the image display and manipulation system 164 for adjustment, storage, and/or display.

The image display and manipulation system 164 may eliminate artifacts from the image(s) and/or may also modify or alter the image(s) based on input from the operator console 110 or other image requirements, for example. The image display and manipulation system 164 may store the image(s) in internal or external memory, for example, and may also display the image(s) on a television, monitor, flat panel display, LCD screen, or other display, for example. The image display and manipulation system 164 may also print the image(s).

The patient positioner 150 allows an object, such as a patient, for example, to be positioned between the target ring 130 and the detector ring 140. The patient positioner 150 may be a table, a table bucky, a vertical bucky, a support, or other positioning device, for example. The patient positioner 150 positions the object between the target ring 130 and the detector ring 140 such that x-rays emitted from the target ring 130 after the sweep of the electron beam pass through the object on the way to the detector ring 140. Thus, the detector ring 140 receives x-rays that have passed through the object. The patient positioner 150 may be moved in steps or discrete distances. That is, the patient positioner 150 moves a certain distance and then stops. Then the patient positioner 150 moves again and stops. The stop-and-go motion of the patient positioner 150 may be repeated for a desired number of repetitions, a desired time, and/or a desired distance, for example. Alternatively, the patient positioner 150 may be moved continuously for a desired time, a desired number of electron beam sweeps of the target ring 130, and/or a desired distance, for example, or the patent positioner 150 may not move.

In operation, a user positions an object, such as a patient, on the patient positioner 150. Then the user selects when to trigger the scan using the operator console 110. In certain embodiments, the scan is triggered based on an R-wave signal from the patient. The user may select a certain predetermined point, phase or percentage of an R-to-R interval between cardiac R-waves at which to begin the scan to acquire image data. That is, a point or trigger is selected to indicate at what point in time the electron beam begins a sweep of the target ring 130. For example, the user may select a trigger at 0% (i.e., the electron beam sweeps the target ring 130 at the start of the R-to-R interval), 40% (i.e., the electron beam sweeps the target ring 130 less than half-way through the interval between R-waves), 80%, and the like. The electron beam scan is triggered after a predetermined period of time (such as 100 milliseconds 130 milliseconds, or 150 milliseconds, for example), at a predetermined point in the R-to-R interval between R-waves (0%, 40%, 80% of the interval, for example), or other predetermined criteria, for example. For example, the user may select a trigger at 130 milliseconds after a reference point in time, such as system start-up, electron beam power-up, patient heartbeat, or other such event. The electron beam in the system 100 may also execute continuous sweeps. That is, the electron beam does not wait for a trigger to sweep the target ring 130 but rather executes repeated sweeps of the target ring 130. Additionally, the electron beam may sweep as many times as the user programs or selects.

Image data may be acquired during a certain time period, such as 50 milliseconds or 100 milliseconds, for example. Then, the sweep(s) may stop. Next, the patient positioner 150 may be moved by the positioner control system 155. For example, a patient on a table may be advanced through the space between the detector ring 140 and the target ring 130. In certain embodiments, the object on the patient positioner 150 may not be scanned while the patient positioner is moving. After the patient positioner 150 has moved, the electron beam may again be triggered at a predetermined percentage of the R-to-R interval, and imaging may begin again. In other embodiments, the patient may be moved during an image scan.

For example, a human operator may choose to trigger at 40% of an R-to-R interval. The operator may select a 40% trigger using the operator console 110. The operator console 110 transmits imaging parameter information to the beam control system 120. The ECG digitizer 122 triggers at the R-wave, and the beam control system 120 wait to trigger the electron beam to begin a sweep of the target ring 130 until 40% of the period between R-waves of the patient's heartbeat is measured. After a sweep of the target ring 130, the patient positioner 150 is advanced. Then, the next sweep begins at 40% of the next R-to-R interval.

In certain embodiments, a contrast agent may be administered to a patient on the patient positioner 150. The beam control system 120 waits for the contrast agent to reach the patient's heart. The beam control system 120 first sweeps the electron beam in a pre-scan of the patient to obtain background data. Then, at the desired point in the heart's R-to-R interval, the electron beam begins sweeping the target ring 130. The sweep may be set to stop before a desired end percentage in the R-to-R interval. Then the table is moved. Next, a subsequent sweep may be obtained. In certain embodiments, sweeps are obtained during three cardiac cycles, for example.

Optionally, the system 100 may scan continuously. That is, the electron beam sweeps the target ring 130 and the DAS 160 collects data from the detector ring 140 without triggering by the ECG digitizer 122 and the beam control system 120. The system 100 scans through a patient's heart continuously for a certain time period as the patient positioner 150 is moving. Hence, all cardiac phases and all slices are imaged in a continuous scan. The system 100 may scan continuously at a rate such that the patient positioner 150 is moving at a rate of one image slice thickness per heartbeat. Therefore, all of the phases and all of the heartbeats of the heart may be obtained.

For example, to obtain an image slice, one target ring 130 is swept. X-rays from the target ring 130 are received by two rows of detectors in the detector ring 140. The patient positioner 150 is advanced at a rate of three millimeters per second, for example. In approximately thirty seconds image data for all slices of a patient's heart and all cardiac phases of the heart may be obtained, for example.

A plurality of images may be obtained during a desired number of sweeps and a desired number of heartbeats. Then, a cine loop of motion video may be created from the obtained images using the image reconstruction module 162 and the image display and manipulations system 164. In certain embodiments, the image reconstruction module 162 may perform interpolation between the rows of detectors in the detector ring 140 to compensate for data falling between the parallel rows. Several slices through a heart are obtained, covering every cardiac phase. For example, the heart is scanned in 6, 3 or 1.5 millimeter slices. The slices are then combined to create a cardiac image.

The electron beam sweeps the stationary target ring 130 in 50 milliseconds, for example. Optionally, the electron beam may sweep faster or slower. A full revolution is traversed in approximately 56 milliseconds (50 milliseconds to sweep the target ring 130 and 6 milliseconds to finish the 360-degree circle of the sweep), for example. A full revolution may be traversed in a greater or lesser amount of time. The DAS 160 acquires image data from the detector ring 140 after electron beam sweeps in order to create an image.

The system 100 may acquire multiple images for a single R-to-R interval. For a typical heart rate of 60 beats per minute (60,000 milliseconds), the DAS 160 may acquire approximately 18 sweeps per R-to-R interval, for example. Using two detector rings 140, 36 completely distinct images may result, 18 images at different ECG phases, and 36 different levels of the heart, for example. The total number of levels of the heart that are scanned may depend on the pitch or speed of the patient positioner 150. The system 100 may trigger sweeps prospectively, or in advance of event occurrence, or the system 100 may trigger retrospectively. The sweeps may be executed in 17 milliseconds, with a 33 millisecond sweep speed being a sweep speed that may remove motion artifacts due to heart motion, for example. For the 33 millisecond case (with a 38 millisecond total sweep time), the system 100 may acquire up to 26 sweeps for a 60 beats-per-minute patient, resulting in 26 different phases and 52 different levels for each R-to-R interval, for example.

Cine imaging is triggered in steps based on an ECG R-wave. A single image data acquisition may be obtained per heartbeat. A single acquisition per heartbeat covers a range of cardiac phases. A patient on the patient positioner 150 is stationary during image acquisition. The patient positioner 150 moves between each image acquisition. A cine-type image set is produced.

Distinct image data acquisitions are obtained per heartbeat. Distinct acquisitions per heartbeat may cover distinct phases of the cardiac cycle. A low dose may be used when attempting to acquire data at clinically significant systole and diastole phases of a heart.

Sweeps may be triggered in different ways based on different criteria. Triggering may be manually activated, predetermined at certain defined percentages of an R-to-R interval or an individual R-wave, set for certain time intervals after reference points in time, or set separately for each sweep. Thus, each sweep of the target ring 130 may be independently configured.

Figure 11:
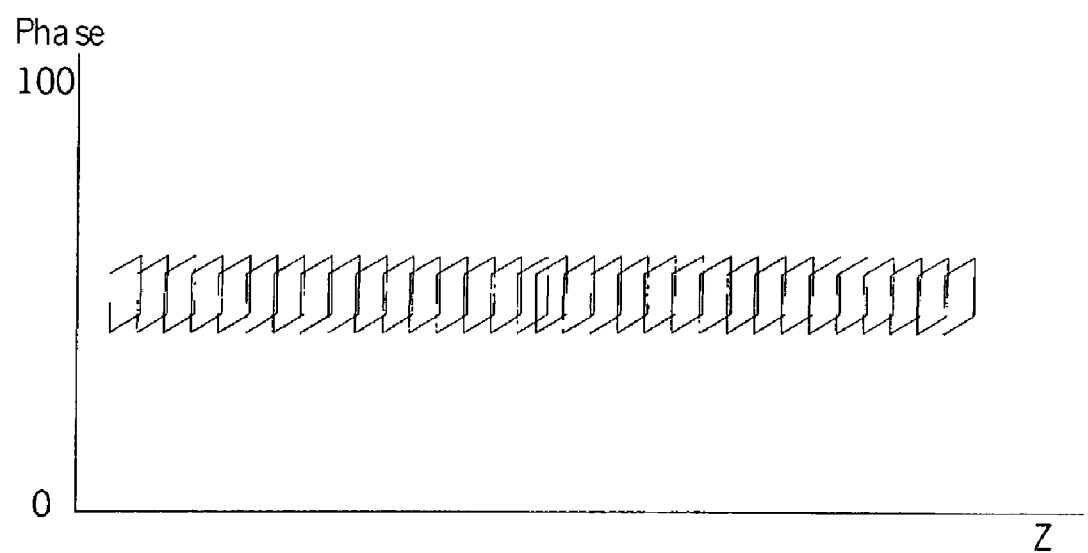
FIG. 11 shows a single phase of the cardiac cycle imaged at each position in accordance with certain embodiments of the present invention.
Figure 12:
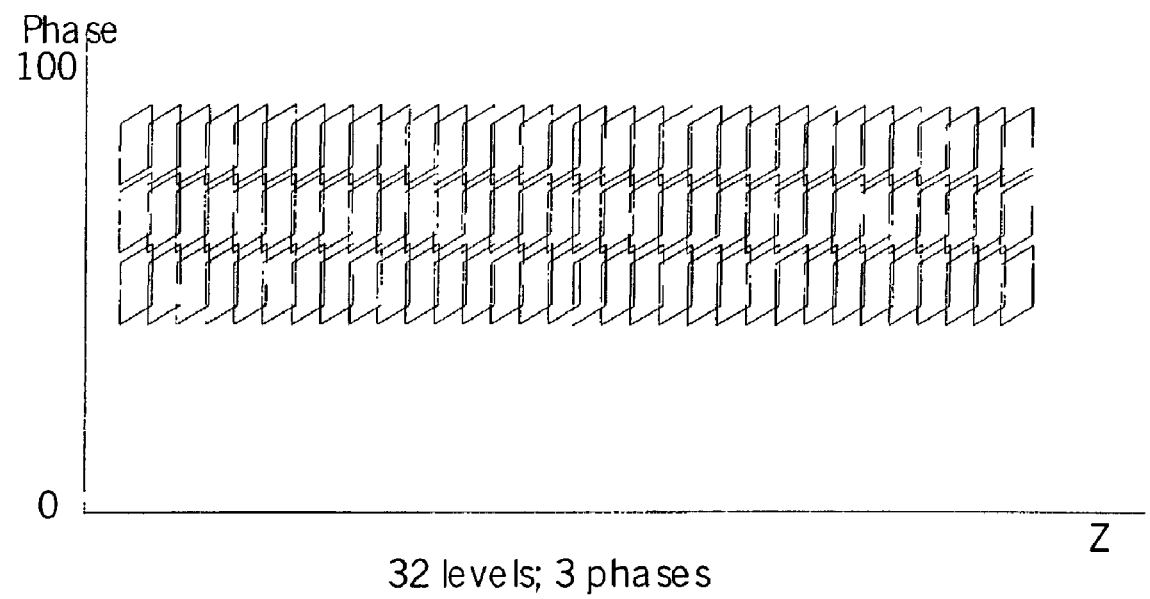
FIG. 12 illustrates utilizing an available time gap to acquire up to three phases in each heartbeat in accordance with certain embodiments of the present invention.
Figure 13:
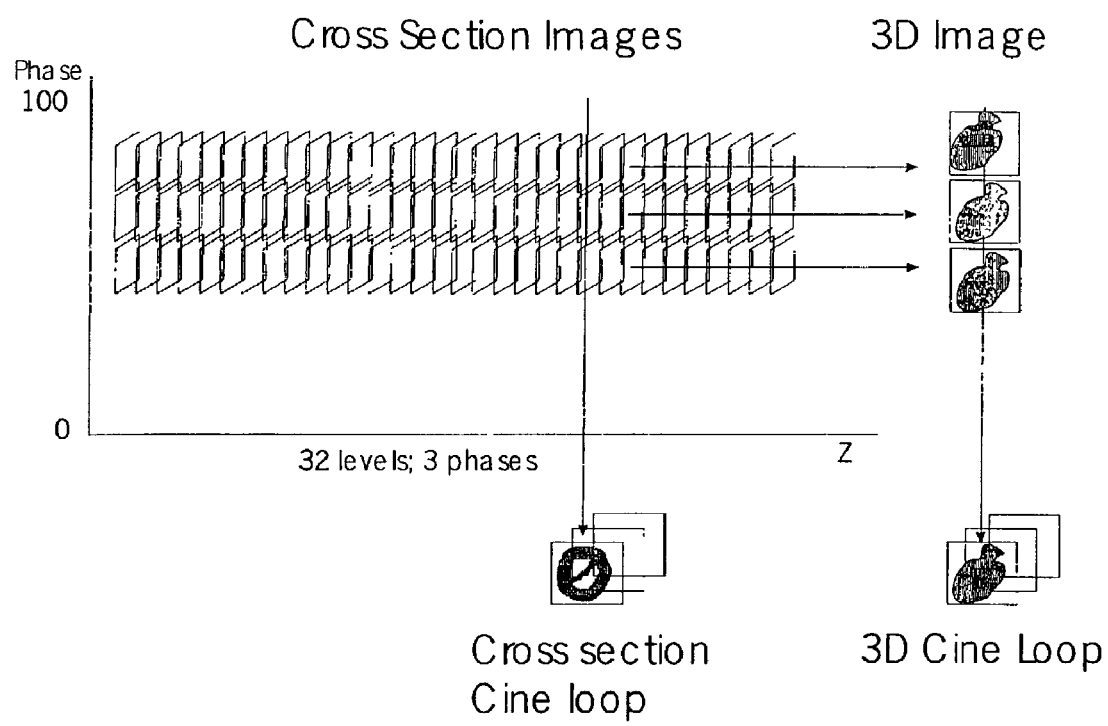
FIG. 13 illustrates a series of cardiac images acquired at 32 levels and 3 phases per level in accordance with certain embodiments of the present invention.
Figure 14:
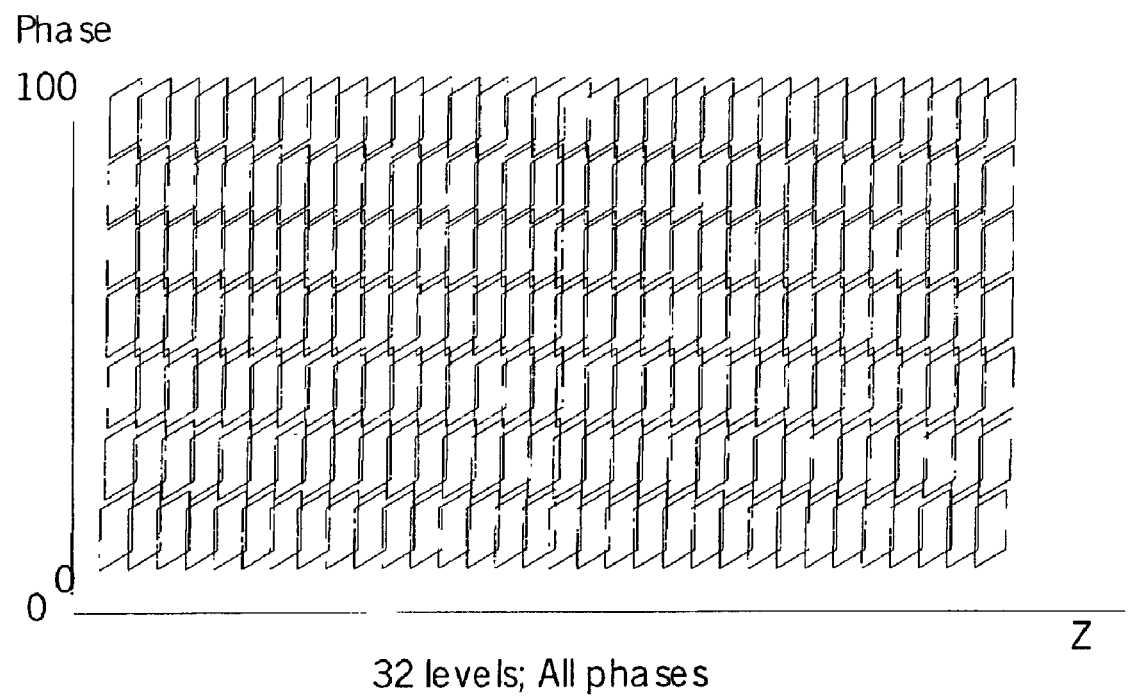
FIG. 14 depicts acquiring all cardiac phases for each heartbeat using continuous volume scanning with two or more multi-detector arrays in accordance with certain embodiments of the present invention.

In the prior art, as shown in FIG. 11, a single phase of the cardiac cycle is imaged at each position. For a single slice scanner, each image is obtained at a consecutive heartbeat. In FIG. 12, by utilizing an available time gap before moving the patient positioner 150, up to 3 phases may be acquired in each heartbeat. FIG. 13 illustrates a series of cardiac images acquired at 32 levels (x-axis) and 3 phases per level (y-axis). On the right are 3 static 3D images that may be rendered from each phase. The 3 images are then combined to produce a cine loop that may display the same information about moving coronary arteries usually obtained by invasive cine-coronary-angiography. Thus, either cross section cine loops or a full 3D cine loop may be formed. Additionally, in a certain embodiment, depicted in FIG. 14, all cardiac phases may be acquired for each heartbeat using continuous volume scanning with two or more multi-detector arrays.

The following example illustrates ECG triggering in certain embodiments of the system 100. Electrodes are placed on a patient's chest and connected to an ECG monitor. The ECG monitor may be a separate unit or may be integrated into the ECG digitizer 122, for example. The ECG monitor may display a moving, real-time ECG wave to aid in placing the electrodes. The ECG monitor may display a recent heart rate based on the R-to-R interval. An R-wave is the primary hump in an ECG wave. The time between R-waves represents the R-to-R interval. The ECG monitor generates a R-wave trigger. The trigger is output to the ECG digitizer 122 for triggering. The ECG monitor also outputs a constant analog datastream of the ECG waves. The datastream may be captured and digitized by the ECG digitizer 122. The digitized waveforms and sweep timing indications may be attached to resulting patient images.

A user may choose when to execute the image scans relative to the R wave and the R-to-R interval. First, the user may choose heartbeats on which to trigger (i.e., whether or not to skip heartbeats). Certain embodiments allow the user to specify different heartbeats for every trigger. For example, the user may choose to trigger on every heartbeat for the first five sets of sweeps, then skip a beat for the next four sets of sweeps, then skip three beats for sets ten through twenty. Second, the user may choose a delay after the R-wave to trigger. The delay may be based on milliseconds, for example. The delay may be a percentage of the R-to-R interval. Selection options may be based on sweep speed. For example, for a 100 millisecond sweep speed, the user may choose delays in percentage between 40% and 80% completion of the R-to-R interval between consecutive R-waves. For a 100 millisecond sweep speed, the user may also choose delays in milliseconds between 246 milliseconds and 999 milliseconds from a reference point in time such as electron beam power-up, system start-up, patient heartbeat, previous R-wave, or other event, for example. For a 50 millisecond sweep speed, the user may choose a delay in percentage at 0% and/or between 40% and 80%, for example. The user may also choose a delay in milliseconds for a 50 millisecond sweep speed at 0 milliseconds and/or between 130 milliseconds and 999 milliseconds from a reference point in time, for example. The user may also choose other settings such as combinations of the number of sweeps per trigger, number of target rings, and sweep speeds to be executed in succession as part of a series description, for example.

The user may also choose to move the patient positioner 150, on which the patient is positioned, between triggers. In certain embodiments, the patient positioner 150 may be moved in differing increments per sweep or per trigger, for example. The patient positioner 150 may be moved between triggers in order to create a volume-type series of images. Not moving the patient positioner 150 between triggers may create a flow-type series of images. When patient positioner 150 motion is indicated, the time of patient positioner 150 motion may be related to the patient heart rate in order to slow the motion of the patient positioner 150. Slowed patient positioner 150 motion related to heart rate may increase patient comfort for series with either short scan times (i.e., one sweep per level), for series that skip heartbeats, or for patients with slow heart rates, for example. Slowed patient positioner 150 motion may also reduce patient positioner 150 motion-induced artifacts in resulting images.

The user may also choose to perform scans on multiple target rings 130. Each target ring 130 may be aligned for a particular detector ring 140 or multiple target rings 130 may be arranged with respect to multiple detector rings 140. Scans on multiple target rings 130 may be performed in a flow-type series (for example, scanning target rings A, B, C, and D in the order DCBA, DBCA, etc.). Scans on multiple target rings 130 may also be performed in a cine-type series (for example, scanning target rings in the order DDDD, CCCC, BBBB, AAAA, etc.). The first sweep of the target rings 130 may be triggered as described above.

When a scanning protocol and user options have been accepted at the operator console 110 and downloaded to the beam control system 120, a median patient heart rate may be calculated. The median heart rate is based on the previous seven heartbeats. The median heart rate may be used to help predict future sweep parameters, such as for timing motion of the patient positioner 150. The median heart rate may also be used to help determine whether heartbeats may be skipped in imaging sweeps, and/or to warn of an inability to achieve a desired cardiac phase for triggering.

The user may then presses a Start button or other initiation key, for example, to being triggering. Optionally, a timed delay or other delay may occur after the Start button is pressed before the start of the first trigger. Next, the scan executes to completion. Optionally, the scan may be paused throughout the process.

Images may be displayed at the image display and manipulation system 164 as soon as available. After a series of images is complete, ECG data collection by the DAS 160 may be halted and uploaded to the image reconstruction module 162. The DAS 160 may insert into the collected data indications of when the sweeps actually occurred. The ECG data set and sweep indications may be attached to the image data. ECG waveforms with trigger indications may be viewed by a user via the image display and manipulation system 164.

When the electron beam is turned off during a scanning series, a delay may occur before the electron beam is used again. The delay associated with electron beam warm up or initialization may be 130 milliseconds or 80 milliseconds. If the electron beam is to be triggered at a time less than the electron beam initialization delay, prediction algorithms are implemented to anticipate when the next R-wave will occur. Such prediction algorithms ensure that the electron beam is generated by the high voltage generator 124 and the beam control system 120 in time for the trigger event.

Figure 2:
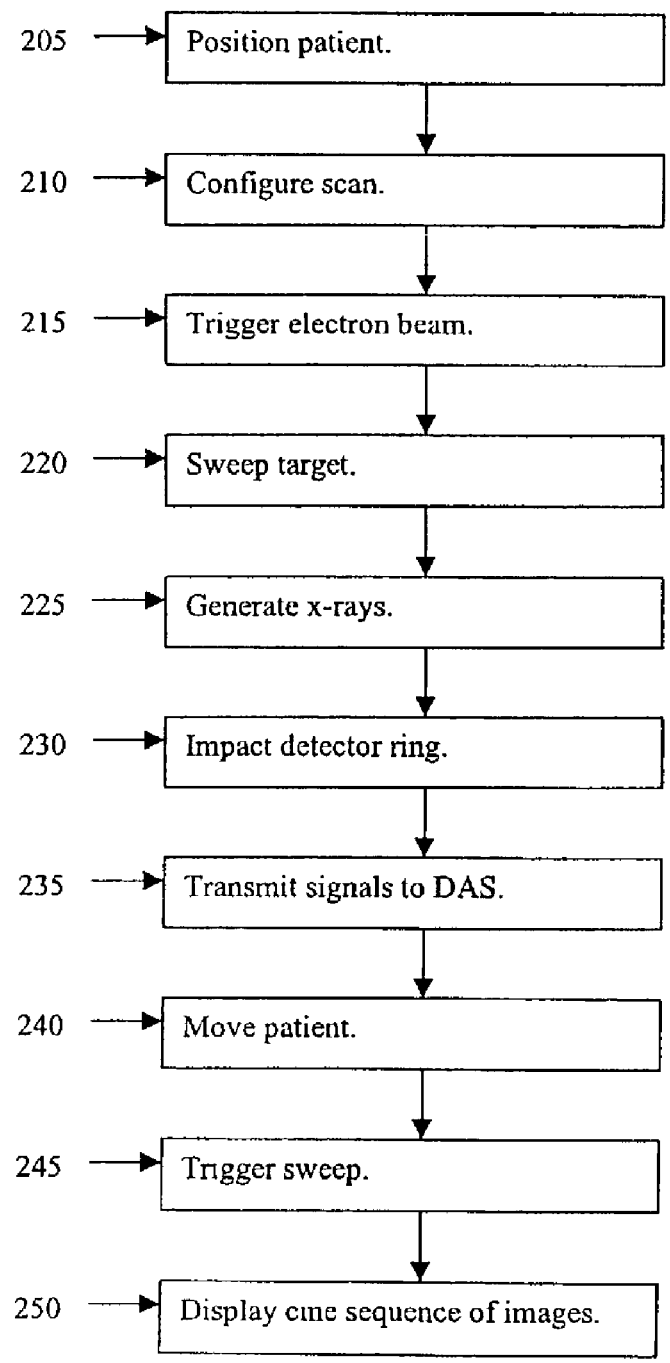
FIG. 2 illustrates a flow diagram for a method for obtaining motion images of coronary activity in accordance with an embodiment of the present invention.

FIG. 2 illustrates a flow diagram 200 for a method for obtaining motion images of coronary activity in accordance with an embodiment of the present invention. First, at step 205, a patient is positioned on a patient positioner 150 or support, such as a table, in an EBT imaging system. Then, at step 210, an operator inputs configuration information for the imaging scan, such as triggers for electron beam sweeps, radiation dosage, timing, number of sweeps, resolution, and/or other configuration information. The operator selects an electron beam trigger based on percentage or phase, such as at 40% completion of an R-to-R interval. Alternatively, the operator may select continuous imaging. The operator also selects step-wise, none or another type of table motion between electron beam sweeps. Optionally, the operator may select continuous table motion during scanning, for example.

Next, at step 215, an energy beam, such as an electron beam, is triggered to sweep the target ring 130. The electron beam may be triggered at a predetermined point in a cardiac R-wave, a time interval from a reference point in time, and/or a defined point in the R-to-R interval between R-waves or R-wave peaks. For example, the beam sweep may be triggered at 40% completion of an R-to-R interval. At step 220, the electron beam sweeps the target ring 130 in an arc. The electron beam may sweep in a 360-degree arc with 210-degrees of the 360-degree arc occupied by the target ring 130.

Then, at step 225, as the electron beam impinges upon the tungsten target ring 130, the tungsten material is excited by the electron beam. X-rays or other such radiation are produced from the excitation and travel outward from the target ring 130. The path of the x-rays depends upon the angle at which the electron beam impacted the target ring 130. At step 230, at least some of the x-rays pass through the patient and impinge upon the detector ring 140.

At step 235, the data acquisition system (DAS) 160 receives signals from the detector ring 140 that are indicative of x-rays impacting the detector ring 140. The received data signals vary in value depending upon the angle and intensity of the x-rays striking the detector ring 140. A larger data value indicates an x-ray that is only slightly attenuated along the x-ray's path from the target ring 130 to the detector ring 140. A smaller data value indicates an x-ray that is greatly attenuated by an organ or other dense mass when travelling from the target ring 130 to the detector ring 140. When no data value is received for a certain portion of the detector ring 140, this indicates that the x-rays impacted bone in the patient and are totally blocked. The DAS 160 transmits the image data to other processing units for further processing and display. The DAS 160 may transmit supplemental data as well, such as ECG data, timing information, triggering information, and/or patient information. Alternatively, the DAS 160 may process the image data. The image data from a single sweep forms a complete image frame.

At step 240, the patient may be moved between or during electron beam sweeps. If moved between sweeps, the patient may be moved by the thickness of a slice (e.g. 1.5 millimeters, 3 millimeters, 6 millimeters, etc.). Alternatively, the patient may be moved continuously during imaging (3 eg. at a rate of 1.5 millimeters, 3 millimeters or 6 millimeters per second). Then, at step 245, after the desired motion has occurred, another sweep may be triggered. For example, after the patient has been moved three millimeters, another electron beam sweep may be triggered at 40% of the next R-to-R interval. The steps described above may be repeated for another sweep. Finally, at step 250, after a desired number of sweeps have been executed and imaging data obtained and processed for a sequence of image frames, the image frames may be displayed as a cine loop. The cine sequence may also be stored or printed. In certain embodiments, the desired number of sweeps are executed in two or more cardiac cycles. The process described above in reference to FIG. 2 may be repeated if desired.

Figure 3:
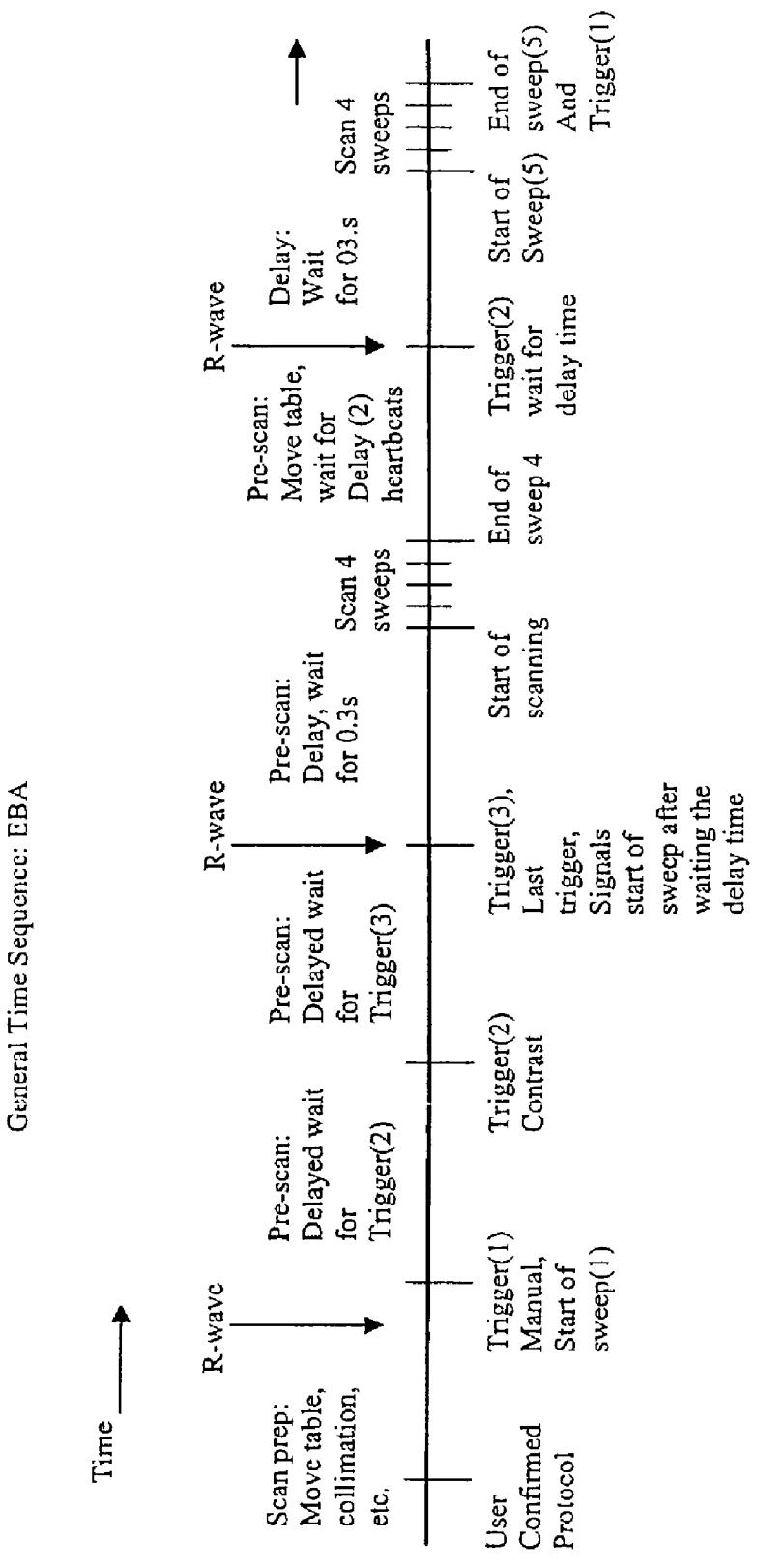
FIG. 3 illustrates an ECG-triggered step-cine sequence as used for electron beam angiography in accordance with certain embodiments of the present invention.

FIG. 3 illustrates an ECG-triggered step-cine sequence 300 as used for electron beam angiography in accordance with an embodiment of the present invention. The sequence 300 involves a contrast injection. The sequence 300 uses an ECG-trigger with a 0.3 second R-to-R interval delay. Also, the sequence 300 uses every heartbeat for scanning unless the heart rate rises above a certain speed threshold. Additionally, the sequence 300 uses a 50 millisecond sweep, performing 4 sweeps per level of the heart (equals 8 slices/level with a dual-slice detector ring). The sequence 300 employs a 3.0 millimeter forward table motion between sweeps.

First, the system 100 is prepared for an image scanning sequence. The patient positioner 150 is moved into position. The electron beam is first triggered (Trigger(1)) after a certain point in an R-to-R interval for pre-scan configuration. A pre-scan may be used to configure or calibrate the system 100 and obtain patient position and other such information. Then, a contrast agent is injected into the patient and the system 100 delays to wait for the second trigger (Trigger(2)). After Trigger(2) triggers a second pre-scan, a delay is observed to prepare the system 100 for another pre-scan. Then, Trigger(3) triggers at the start of an R-wave for the third pre-scan. After a 0.3 second delay, four imaging sweeps of the target ring 130 are executed. After the fourth sweep, the patient positioner 150 is moved 3.0 millimeters. The system 100 waits for two heartbeats. Then, the electron beam is triggered at a selected point in an R-wave. After a delay (e.g., 03 . . . seconds), four more sweeps of the target ring 130 are executed.

A cine loop may be created from image data obtained during the sweeps of the target ring 130. Image frames are formed from data obtained during a sweep of the target ring 130. The image frames may be displayed individually or displayed in sequence to show cardiac motion. Cine imaging is used to animate the images and create a 2-D or 3-D effect.

FIG. 4 illustrates an example of a sweep map 400, which describes a scanning series in a sweep-by-sweep format in accordance with an embodiment of the present invention. The sweep map 400 is described as follows. The sweep row in the map 400 represents a sweep number from 1 to 8. The sweep number may repeat according to the number of slices and levels chosen. The coll row in the map 400 represents collimation in the system 100. In the map 400, a collimation of 3 indicates the use of dual 1.5 mm slices in scanning. The mA row indicates a desired number of milliamps to drive the electron beam, for example 1000 mA. The characteristic kV indicates a desired kilivoltage for the electron beam, such as 140 kV, for example. The Det parameter in the map 400 represents a number of detector rings 140 in the system 100. A value of 3 in a two detector ring 140 system 100 indicates that both detector rings 1 and 2 are used. Type represents a type of sweep to be executed. In certain embodiments, a value of 3 indicates a sweep speed of 50 milliseconds, for example. Horiz indicates horizontal position of the patient positioner 150. In the map 400, a value of 400 indicates a 400 millimeter position relative to a user-defined zero position. A value of 397 indicates 397 millimeters, which implies that the patient positioner 150 moved back 3.0 millimeters between triggers. Vert is patient positioner 150 vertical position, such as 210 millimeters, for example. Slew is patient positioner 150 slew, or lateral movement beside the plane of motion. A slew of 0 degrees indicates no slew. Tilt is a tilt of the patient positioner 150, representing movement within the plane of motion. A tilt of 0 degrees indicates no tilt. The row labeled Table Incr lists an increment of patient positioner 150 motion during each sweep. A table increment of 0 at sweep=0 indicates that the table did not move during scanning in sweep 0, for example. Target represents a type of target ring 130. For example, Target=3 indicates a C-ring target.

The Trigger row in the map 400 reflects an array indicating trigger type. A trigger type array may be in the form of Trigger=(a,b,c,d), for example. For example, in sweep 1 of the map 400, Trigger=(5,1,7,5,9), wherein 5 equals the total entries into the trigger array; 1 indicates that a manual trigger is to be a first trigger; 7 instructs the system 100 to wait for a bolus injector trigger to be a second trigger; 5 represents the minimum number of beats to skip and directs to choose the first available trigger; and 9 indicates that a timed delay may be used after an R-wave. In sweep 5, Trigger=(4,8,5,9). Thus, there are 4 entries into the array. Array element 8 indicates that table motion is completed before a scan. Array element 5 indicates that the first available trigger may be chosen. Array element 9 instructs the system 100 to use a timed delay after an R-wave.

The Delay row in the map 400 represents a delay array associated with the trigger array. For example, Delay=(a,b,c,d). In sweep 1 of the map 400, for example, Delay=(5,0, 16,0,0.3), wherein 5 indicates 5 total entries in the delay array; 0 indicates 0 seconds timed delay after a manual trigger; 16 indicates a timed delay of 16 seconds after a bolus injector trigger; 0 determines that 0 skipped heartbeats is a minimum number to skip based on thermal modeling, sweep times, table step minimum times, and reasonable heart rate, for example; and 0.3 represents a 0.3 second delay after an R-wave to start sweep 1. In sweep 5 of the map 400, Delay=(4,0.25,0,0.3). A value of 4 indicates 4 entries in the Delay array. A value of 0.25 relates to a 0.25 second minimum patient positioner 150 step time between sweeps. A value of 0 in the third array position indicates a minimum of 0 skipped heartbeats. A value of 0.3 in the last position indicates a 0.3 second delay after an R-wave to start a sweep, for example.

Figure 5:
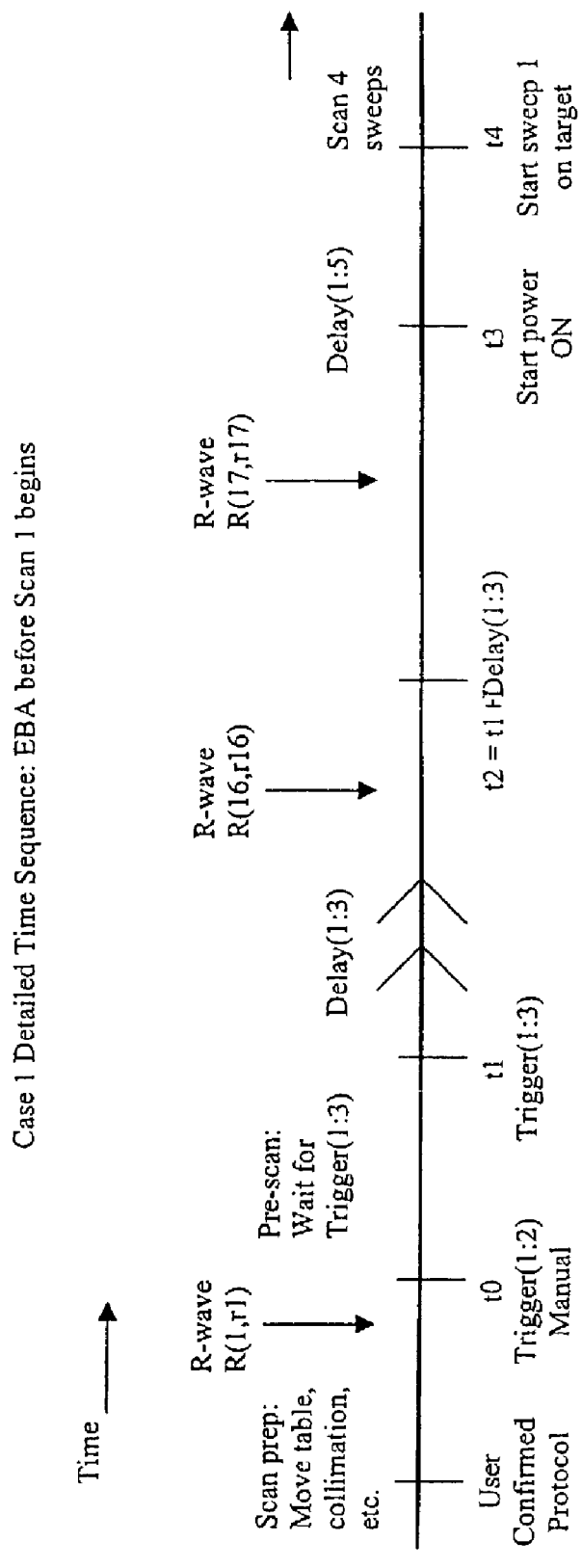
FIG. 5 illustrates a time sequence before a scan 1 begins, in accordance with certain embodiments of the present invention.
Figure 6:
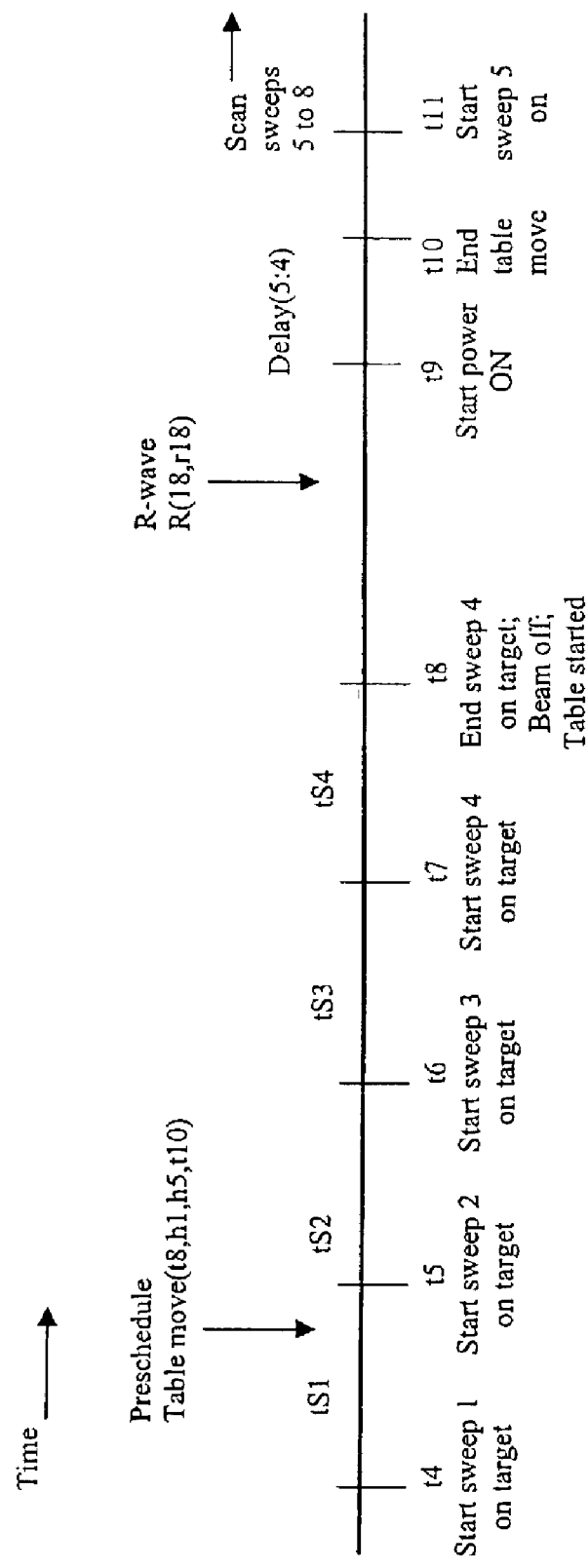
FIG. 6 illustrates a time sequence between a sweep 1 and a sweep 2, in accordance with certain embodiments of the present invention.

FIGS. 5 and 6 illustrate an EBA scanning series in accordance with certain embodiments of the present invention. In FIGS. 5 and 6, the electron beam may be turned on after an R-wave has been detected. That is, FIGS. 5 and 6 depict a scan execution in which a delay after an R-wave is less than or equal to the time period for electron beam power up.

FIG. 5 illustrates a time sequence 500 before scan 1 begins, in accordance with certain embodiments of the present invention. In FIG. 5, a sweep includes activities before the sweep plus a traversal of the target ring 130. The notation Trigger(1:3) indicates that the trigger for sweep 1 is the third element in the Trigger array. In the time sequence 500, Trigger(1:3)=7, which indicates a bolus injection, for example. Time stamps are indicated by tn, where n may increment. For example, the first time stamp is t0. R-waves may be shown as R(n,rn), where n may increment as R-waves are collected and rn is a time at which the nth R-wave appeared. In the time sequence 500, t0 is the clock time at manual trigger. Time stamp t1 is the clock time at the bolus injector trigger. Time stamp t2 may be calculated as the t1+Delay(1:3), or t1+16 seconds, for example. In the time sequence 500, Delay(1.4) is 0 (no skipping), so R-wave R(17,r17) may be used to start scanning. Time stamp t3=r17+Delay(1:5) timePSon=r17+0.3 seconds−0.130 seconds. Time t4−17+Delay(1:5)=r17+0.3 seconds.

In the time sequence 500, after the first R-wave R(1,r1), the system 100 begins pre-scan configuration and calibration. After a bolus injection of contrast agent at t1, the system 100 may wait for the agent to affect the heart and coronary arteries. Then, after R-wave R(17,r17), the electron beam may be powered on and a series of four sweeps begun on the target ring 130. The series of sweeps will be illustrated in FIG. 6 below.

FIG. 6 illustrates a time sequence 600 between sweep 1 and sweep 2, in accordance with certain embodiments of the present invention. Assuming the same delay parameters (delay>power on time) are used from the start of sweep 1 to the start of sweep 5, the same timing may be used on each subsequent trigger. In the time sequence 600, time taken during a sweep is represented as tSn, where n increments with the sweep number. Time intervals tm equal the previous time interval tm−1 plus the time taken during the previous sweep. For example, in the time sequence 600, the time to start sweep 2 is defined as t5. In time sequence 600, t5 t4+tS1. Time during a sweep in sequence 600 represents total sweep time, including retrace-on, target time, and retrace-off time, for example. Horizontal table positions may be sent to the patient positioner 150 as they appear in the sweep map 400 and are represented as hn, where n is the sweep number. In time sequence 600, table position h1 is the position of the patient positioner 150 during sweep 1 and is equal to 400. Table position h5 is the patient positioner 150 position during sweep 5 and is equal to 397 (a movement of 3.0 millimeters).

In the time sequence 600, four sweeps of the target ring 130 are executed over intervals tS1 through tS4, beginning at time stamp t4. Image data is obtained from each sweep. At time stamp t8, the electron beam is turned off. Additionally, the patient positioner 150 may be moved after sweep 4. After a certain point in the R-wave R(18,r18), the electron beam may be powered on again. After a certain delay Delay(5:4), the motion of the patient positioner 150 may cease and the next sequence of target ring 130 sweeps may begin. Additional image frames may be generated from the sweeps to form a cine loop of image frames. The image display and manipulation system 164 may combine the image frames into a cine imaging loop displaying motion of the heart and coronary arteries over time and cardiac phase.

Figure 7:
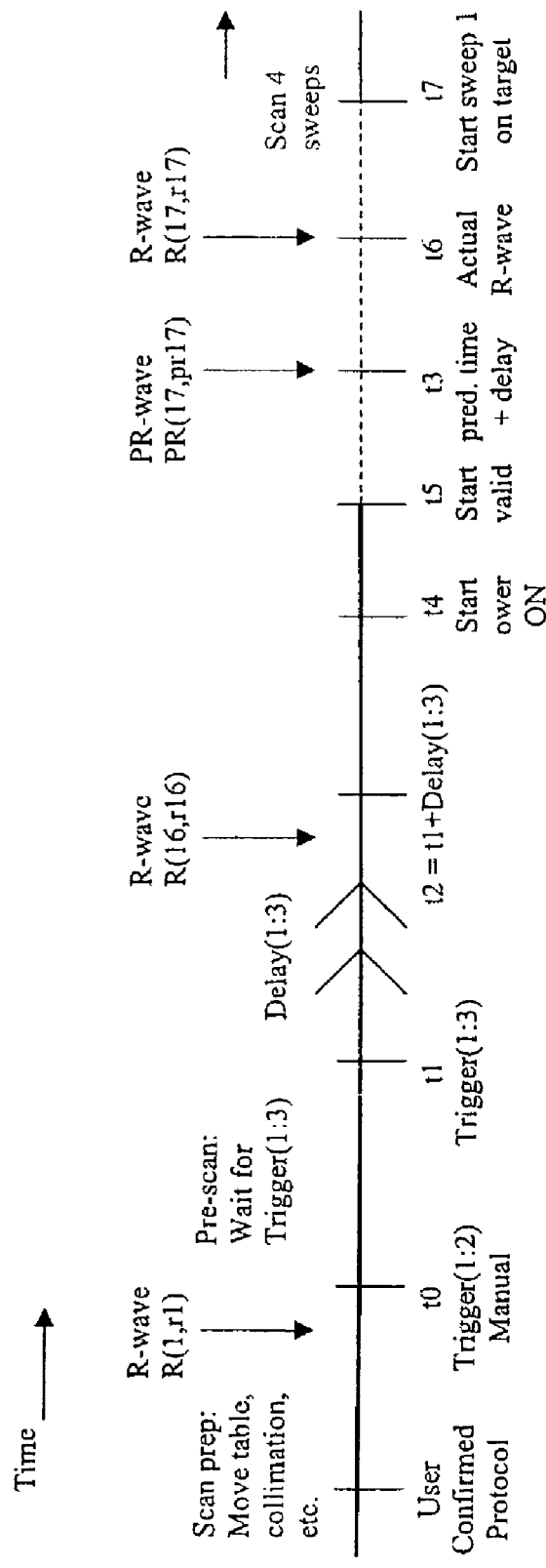
FIG. 7 illustrates a time sequence for a scan from user confirmation to start of a sweep 1 on the target ring in accordance with certain embodiments of the present invention.
Figure 8:
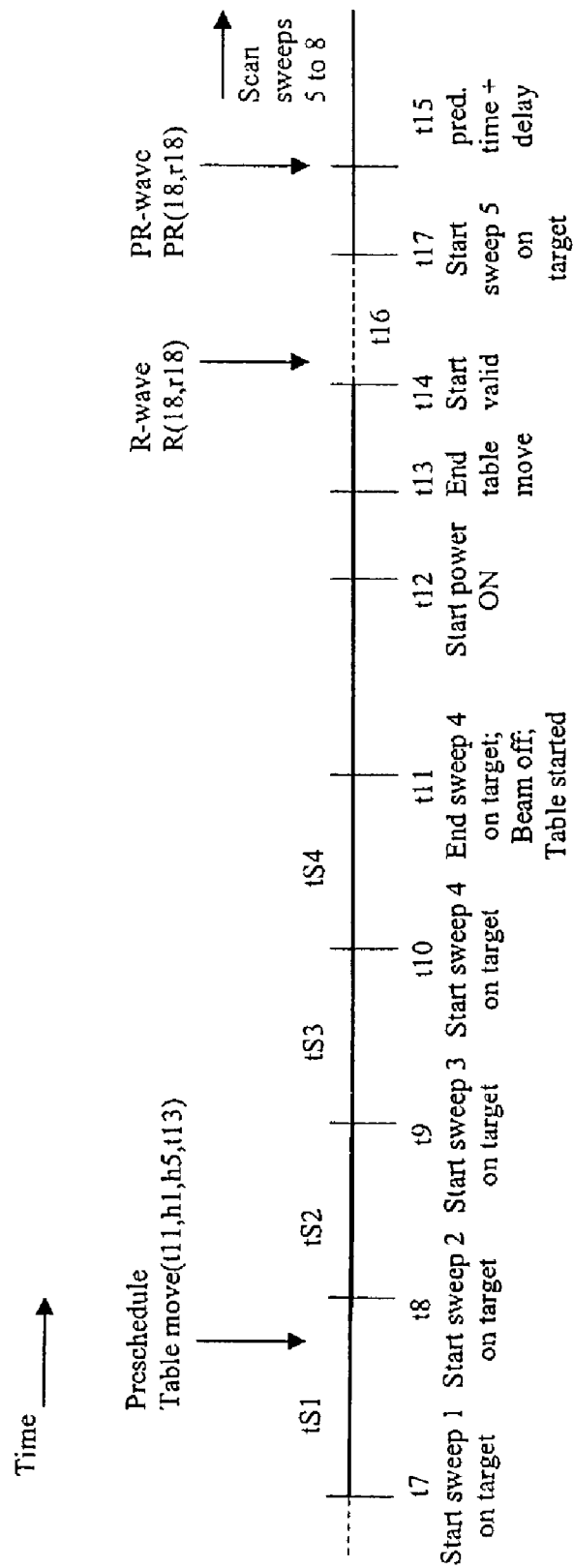
FIG. 8 illustrates a time sequence from start of a sweep 1 on the target ring to start of a sweep 5 on the target ring in accordance with certain embodiments of the present invention.

FIGS. 7 and 8 illustrate image scanning sequences in which a delay chosen is less than the time taken to activate the power supply for the electron beam. In FIGS. 7 and 8, the electron beam is turned on before an upcoming R-wave. That is, FIGS. 7 and 8 depict a scan execution in which a delay after an R-wave is greater than the time period for electron beam power up. If a delay is set less than the electron beam power on time, the high voltage module 124 is turned on in anticipation of the R-wave and delay. If the beam is not turned on early enough or the R-wave comes unexpectedly early, the beam may not be ready to sweep the target ring 130. If the electron beam is not ready to sweep the target ring 130, the beam may be deactivated and the start time recalculated for the next expected R-wave. In certain embodiments, the electron beam may be aimed at a beam stop in anticipation of an R-wave. The beam stop may absorb heat from the electron beam up to a thermal capacity based on the material used for the beam stop. If a valid R-wave does not arrive before the thermal capacity of the beam stop is reached, the series may be aborted and calculations restarted.

FIG. 7 illustrates a time sequence 700 for a scan from user confirmation to start of sweep 1 on the target ring 130 in accordance with certain embodiments of the present invention. The time sequence 700 is similar to the time sequence 500, described above. In the time sequence 700, however, the dotted line indicates electron beam power-on time. The electron beam may be powered-up by focusing it on a beam stop during the period between t5 and t7, indicated by the dotted line, for example. In the time sequence 700, PR(17, pr77) indicates a predicted R-wave time, where n represents a number of heartbeats. The PR(17,pr17)time is used to initiate the electron beam. The time R(17,r17) indicates the actual incidence of an R-wave. After the electron beam is powered on and a delay is observed to allow the electron bream to reach a desired intensity, sweep 1 may be triggered at time t7 at a desired point in the R-wave R(17,r17). If the time between the predicted R-wave PR(17,r17) and the actual R-wave R(17,r17) exceeds a certain threshold, the beam stop may reach a thermal limit. If the beam stop's thermal limit is reached, the series of sweeps may be abandoned and restarted.

FIG. 8 illustrates a time sequence 800 from start of sweep 1 on the target ring 130 to start of sweep 5 on the target ring 130 in accordance with certain embodiments of the present invention. The time sequence 800 continues from the time sequence 700. The time sequence 800 is similar to the time sequence 600, described above. In the time sequence 800, the electron beam is turned on at time t12. During the dotted time period t16 represents electron beam power-on time. A delay may be used to allow the electron beam to power up before another series of sweeps begin. If the heartbeat r18 occurs before the electron beam is valid at time t14, heartbeat r18 may be skipped, and the system 100 may wait for heartbeat r19, unless thermal accumulation at the beam stop exceeds the thermal threshold of the beam stop.

In an alternative embodiment, trigger delays may be calculated using a formula based on patient heart rate. The heart rate may be a heart rate at the start of a series of imaging sweeps or a median heart rate throughout a series of sweeps, for example. Alternatively, trigger delays may be obtained for each trigger based on a lookup table of predetermined values.

Additionally, triggering may be implemented with a pattern of delays and/or patient positioner 150 increments. For example, a first trigger may be executed at 0% after an R-wave and a sweep may acquire a full heartbeat. Then, a second sweep may be triggered at 40% after an R-wave with a small patient positioner 150 move. Next, a third sweep may be triggered at 80% after an R-wave, followed by a larger move of the patient positioner 150.

Furthermore, in an alternative embodiment, an operator may be allowed to pause the system 100. For example, a user may pause the electron beam between sweeps to allow a patient to take a breath. After the patient takes a breath, the user may resume the scanning series, for example.

In an alternative embodiment, multiple sweeps may be executed during a single R-to-R interval. For example, a first sweep may be executed at 40% completion of an R-to-R interval, and then a second sweep of the target ring 130 may be executed after 80% of the R-to-R interval. Thus, multiple images may be obtained in an R-to-R interval. Additionally, the patient positioner 150 may be moved between sweeps. That is, a sweep is triggered at 40%, then the patient positioner 150 is moved after the sweep, and then another sweep is triggered at 80% of the R-to-R interval. The pattern may be repeated with further movement of the patient positioner 150. Thus, two image acquisitions may be obtained per heartbeat (e.g., one image at 40% and a second image at 80%), for example. The images may be used in a cine loop or may be viewed as individual images.

Figure 9:
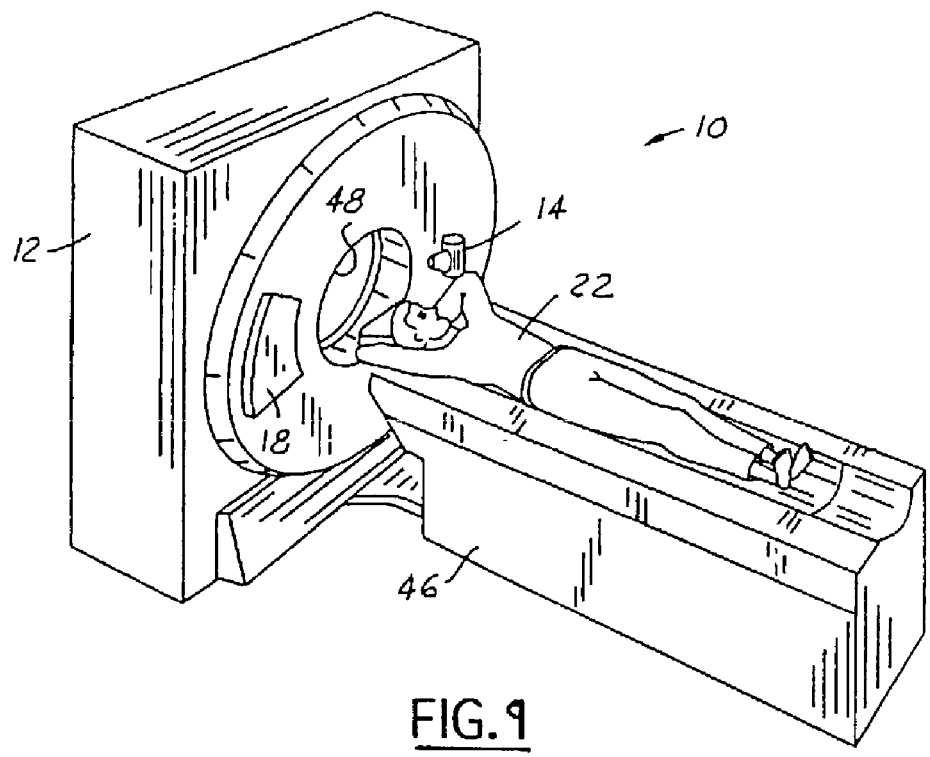
FIG. 9 illustrates a conventional mechanical CT scanner in accordance with certain embodiments of the present invention.
Figure 10:
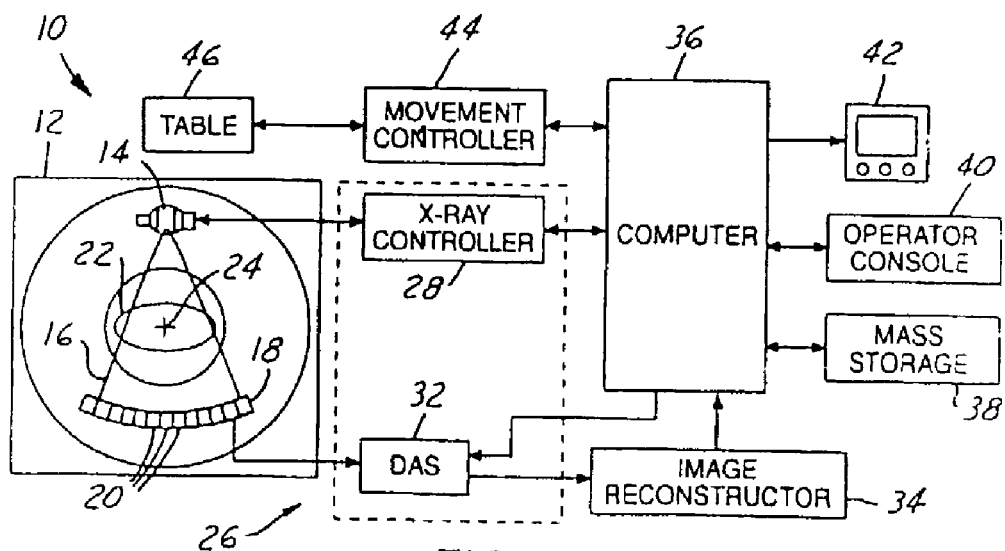
FIG. 10 illustrates a block diagram of a conventional mechanical CT scanner in accordance with certain embodiments of the present invention.

In an alternative embodiment, a conventional mechanical computed tomography scanner may be used for cine imaging. FIG. 9 illustrates a conventional mechanical CT scanner 900 in accordance with certain embodiments of the present invention. FIG. 10 illustrates a block diagram of a conventional mechanical CT scanner 1000 in accordance with certain embodiments of the present invention. FIGS. 9 and 10 illustrate a CT imaging system as described in U.S. Pat. No. 6,385,292 to Dunham et al.

In certain embodiments, a cine angiography series of images may be obtained from a conventional CT scanner, such as the CT scanner described in FIGS. 9 and 10. X-rays from an x-ray source 14 may irradiate a patient 22 and impinge upon a detector 18. The DAS 32 may collect image data based on the x-rays impinging upon the detector 18 and form a cine loop of motion images using an image reconstructor 34 and a computer 36. The patient 22 is positioned on a table 36. The table 43 may be moved during scanning. A cine sequence of images depicting patient cardiac activity may be obtained as described above.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for obtaining cine angiography images with a computed tomography (CT) scanner, comprising:
   monitoring a cardiac cycle of a patient;
   selecting at least one independently configurable trigger array, said at least one trigger array including a plurality of trigger points;
   initiating at least one CT scan of said patient based on said at least one trigger array;
   selecting at least one additional independently configurable trigger array, said at least one trigger array including an additional plurality of trigger points;
   initiating at least one additional CT scan of said patient based on said at least one additional trigger array;
   performing at least two CT scans of said patient during a time period over two or more cardiac cycles; and
   constructing a cine angiography loop from said at least two CT scans.

2. The method of claim 1, wherein said performing step obtains said at least two CT scans during a single cardiac cycle.

3. The method of claim 1, wherein said performing step obtains said at least two CT scans consecutively and beginning at different points within said time period.

4. The method of claim 1, wherein said performing step performs a complete CT scan in no more than 100 milliseconds.

5. The method of claim 1, further comprising sweeping an electron beam across a target ring to perform said at least two CT scans.

6. The method of claim 1, utilizing an x-ray fan beam to obtain said at least two CT scans.

7. The method of claim 1, further comprising combining a series of three dimensional images into a three dimensional cine loop based on said at least two CT scans.

8. The method of claim 1, further comprising displaying a series of moving three dimensional images based on said at least two CT scans.

9. The method of claim 1, wherein said initiating step includes prospective gating based on said cardiac cycle of the patient.

10. The method of claim 1, further comprising moving the patient with respect to the CT scanner between or during CT scans.

11. The method of claim 1, further comprising moving the patient with respect to the CT scanner during each of said at least two CT scans to obtain spiral scan.

12. The method of claim 1, wherein said performing step obtains multiple parallel CT slices from separate parallel rows of detectors in the CT scanner.

13. The method of claim 1, wherein said performing step obtains one image for each CT scan.

14. A method for obtaining cine loop images with a computed tomography (CT) scanner, comprising:
   monitoring a cardiac cycle of a patient;

selecting at least one independently configurable trigger array, said at least one trigger array including a plurality of trigger points associated with two or more events with respect to said patient;

initiating at least one CT scan of said patient based on said at least one trigger array;

selecting at least one additional independently configurable trigger array, said at least one trigger array including an additional plurality of trigger points associated with two or more events with respect to said patient;

initiating at least one additional CT scan of said patient based on said at least one additional trigger array;

performing at least two CT scans of said patient during a time period over two or more cardiac cycles;

sweeping an electron beam along a target to generate an x-ray fan beam to perform at least two CT scans; and constructing a cine angiography loop from said at least two CT scans.

15. The method of claim 14, wherein said sweeping step obtains said at least two CT scans during a single cardiac cycle.

16. The method of claim 14, wherein said sweeping step obtains said at least two CT scans consecutively and beginning at different points within a time period of two or more cardiac cycles.

17. The method of claim 14, wherein said sweeping step performs a complete CT scan in no more than 100 milliseconds.

18. The method of claim 14, further comprising combining a series of three dimensional images into a three dimensional cine loop based on said at least two CT scans.

19. The method of claim 14, further comprising displaying a series of moving three dimensional images based on said at least two CT scans.

20. The method of claim 14, wherein said initiating step includes prospective gazing based on said cardiac cycle of the patient.

21. The method of claim 14, further comprising moving the patient with respect to the CT scanner between or during CT scans.

22. The method of claim 14, further comprising moving the patient with respect to the CT scanner during each of said at least two CT scans to obtain spiral scans.

23. The method of claim 14, wherein said sweeping step obtains multiple parallel CT slices from separate parallel rows of detectors in the CT scanner.

24. The method of claim 14, further comprising performing at least two CT scans of the patient during a time period over two or more cardiac cycles.

25. A method for generating cine angiography images, comprising:

monitoring a cardiac cycle of a patient;

selecting at least one independently configurable trigger array, said at least one trigger array including a plurality of trigger points;

initiating at least one CT scan of said patient based on said at least one trigger array;

selecting at least one additional independently configurable trigger array, said at least one trigger array including an additional plurality of trigger points;

initiating at least one additional CT scan of said patient based on said at least one additional trigger array;

performing at least two CT scans of said patient during a time period over two or more cardiac cycles;

constructing a cine angiography loop from said at least two CT scans; and moving automatically the patient with respect to said CT scanner between or during at least two CT scans.

26. The method of claim 25, wherein said performing step obtains said at least two CT scans during a single cardiac cycle.

27. The method of claim 25, wherein said performing step obtains said at least two CT scans consecutively and beginning at different points within a time period of two or more cardiac cycles.

28. The method of claim 25, wherein said performing step performs a complete CT scan in no more than 100 milliseconds.

29. The method of claim 25, further comprising combining a series of three dimensional images into a three dimensional cine loop based on said at least two CT scans.

30. The method of claim 25, further comprising displaying a series of moving three dimensional images based on said at least two CT scans.

31. The method of claim 25, wherein said initiating step includes prospective gating based on said cardiac cycle of the patient.

32. The method of claim 25, further comprising moving the patient with respect to the CT scanner during each of said at least two CT scans to obtain spiral scans.

33. The method of claim 25, wherein said performing step obtains multiple parallel CT slices from separate parallel rows of detectors in the CT scanner.

* * * * *

UNITED STATES PATENT AND TRADEMARK OFFICE
CERTIFICATE OF CORRECTION

PATENT NO. : 7,020,511 B2 Page 1 of 1
APPLICATION NO. : 10/064756
DATED : March 28, 2006
INVENTOR(S) : Boyd et al.

It is certified that error appears in the above-identified patent and that said Letters Patent is hereby corrected as shown below:

At col. 11, line 35, delete "3 eg." and insert --e.g.--

At col. 12, line 11, delete "03 . . . seconds" and insert --0.3 seconds--

At col. 12, line 38, delete "Iloriz" and insert --Horiz--

At col. 13, line 45, after "(1:5)" insert -- – --

At col. 13, line 46, delete "17" and insert --r17--

Signed and Sealed this

Twenty-second Day of August, 2006

JON W. DUDAS
*Director of the United States Patent and Trademark Office*